United States Patent [19]

Eckert

[11] 3,959,378

[45] May 25, 1976

[54] N-ALKYL-N'-POLYHYDROXYALKYL-ALKYLENE DIAMINES

[75] Inventor: Hans-Werner Eckert, Dusseldorf, Germany

[73] Assignee: Henkel & Cie G.m.b.H., Dusseldorf, Germany

[22] Filed: May 14, 1973

[21] Appl. No.: 359,989

[30] Foreign Application Priority Data

June 2, 1972 Germany ........................2226869

[52] U.S. Cl. ............................ 260/584 R; 252/8.75; 252/8.8; 260/583 P; 260/584 B

[51] Int. Cl.[2] .......................................... C07C 91/10

[58] Field of Search ................................ 260/584 R

[56] References Cited

UNITED STATES PATENTS 3,803,237 4/1974 Lednicer et al..................... 260/584

*Primary Examiner*—Robert V. Hines

*Attorney, Agent, or Firm*—Hammond & Littell

[57] ABSTRACT

A compound of the formula $$R-NH-(CH_2)_n-NH-CH_2-(CHOH)_m-CH_2OH$$

in which R is an alkyl of 8 to 24 carbon atoms, $n$ is an integer from 2 to 6, and $m$ is an integer from 3 to 4; and a one step process for washing and softening textiles using this compound.

7 Claims, No Drawings

N-ALKYL-N'-POLYHYDROXYALKYL-ALKYLENE DIAMINES

THE PRIOR ART

Reaction products of aldoses with long-chain primary amines and long-chain epoxides are known and have been reported as useful as softeners for cotton fabrics. However these prior art textile softeners are not very effective unless the compounds are added to the last rinse bath of the textiles to be treated. The textile softening results attainable with these known compounds in the wash bath is very slight.

OBJECTS OF THE INVENTION

It is an object of the present invention to provide a compound of the formula $$R-NH-(CH_2)_n-NH-CH_2-(CHOH)_m-CH_2OH$$

in which R is an alkyl of 8 to 24 carbon atoms, *n* is an integer from 2 to 6, and *m* is an integer from 3 to 4.

It is another object of the present invention to provide a one-step process for the washing and softening of textiles which consists essentially of immersing soiled textiles in an aqueous softening washing liquor bath at temperatures of from 30° to 100°C for a time sufficient to clean and soften said textiles and recovering said cleaned and softened textiles, said aqueous softening washing liquor bath containing (1) from 0.1 to 3.0 gm/liter of anionic surface active agents and builder salts and (2) from 0.1 to 2.0 gm/liter of an N-alkyl-N'-polyhydroxyalkyl-alkylene diamine of the formula $$R-NH-(CH_2)_n-NH-CH_2-(CHOH)_m-CH_2OH$$

in which R is an alkyl of 8 to 24 carbon atoms, *n* is an integer from 2 to 6, and *m* is an integer from 3 to 4.

These and other objects of the present invention will become apparent as the description thereof proceeds.

DESCRIPTION OF THE INVENTION

The present invention provides a compound of the formula $$R-NH-(CH_2)_n-NH-CH_2-(CHOH)_m-CH_2OH$$

in which R is an alkyl of 8 to 24 carbon atoms, *n* is an integer from 2 to 6, and *m* is an integer from 3 to 4.

The present invention is further directed to a one-step process for the washing and softening of textiles which consists essentially of immersing soiled textiles in an aqueous softening washing liquor bath at temperatures of from 30° to 100°C for a time sufficient to clean and soften said textiles and recovering said cleaned and softened textiles, said aqueous softening washing liquor bath containing (1) from 0.1 to 3.0 gm/liter of anionic surface active agents and builder salts and (2) from 0.1 to 2.0 gm/liter of an N-alkyl-N'-polyhydroxyalkyl-alkylene diamine of the formula $$R-NH-(CH_2)_n-NH-CH_2-(CHOH)_m-CH_2OH$$

in which R is an alkyl of 8 to 24 carbon atoms, *n* is an integer from 2 to 6, and *m* is an integer from 3 to 4.

The compounds of the present invention are produced by the reaction of N-alkyl-alkylene diamines with aldoses of the formulas stated below, in which *n* and *m* have the above defined meaning, and subsequent hydrogenation of the reaction products according to the following reaction equations:

$$R-NH-(CH_2)_n-NH_2 + CHO-(CHOH)_m-CH_2OH$$

$$\downarrow \text{Heating}$$

$$R-NH-(CH_2)_n-NH-CHOH-(CHOH)_m-CH_2OH$$

$$-H_2O \downarrow H_2 \text{ / Catalyst}$$

$$R-NH-(CH_2)_n-NH-CH_2-(CHOH)_m-CH_2OH$$

Suitable examples of the N-alkylalkylene diamines to be used as starting materials are those in which R is alkyl of 8 to 24 carbon atoms and in which the alkylene has 2 to 6 carbon atoms, as follows:

N-Octyl-ethylene diamine, N-octadecyl-ethylene diamine,
N-dodecyl-trimethylene diamine, N-octyl-hexamethylene diamine,
N-docosyl-trimethylene diamine, N-tetracosyl-ethylene diamine,
N-tetradecyl-tetramethylene diamine, N-eicosyl-trimethylene diamine, N-tetradecyl-pentamethylene diamine, and N-decyltetramethylene diamine.

Other suitable examples of N-alkyl-alkylene diamine starting materials are those which may be derived from natural fatty acid mixtures such as coconut fatty acid and tallow fatty acid, for example, N-coconutalkyl-trimethylene diamine, N-tallowalkyl-trimethylene diamine.

Suitable examples of aldoses to be used economically as starting materials are aldopentoses such as arabinose or aldohexoses such as glucose or mamose. For the preparation of technical quality products invert sugar may be used.

The condensation reaction of the above named reactants is usually carried out in a molar ratio of 1:1 by heating to temperatures between 50° and 100°C with addition of a suitable solvent, for example a lower alkanol such as ethanol, and of a hydrogenation catalyst, for example Raney nickel under a hydrogen pressure of 150 to 200 atm. The reaction temperature ranges from 50°C to 100°C and the reaction is preferably regulated so that the beginning of the reaction is carried out in the lower temperature range, and after about one-third of the total reaction time the temperature is raised step by step to the highest temperature.

After removal of the hydrogenation catalyst for example by filtration, the reaction product crystallizes out of the alcohol solution during the subsequent cooling thereof, and can be purified by recrystallization, for example from ethanol.

The compounds of the invention produced as described above are white, fine-crystalline substances, which constitute valuable raw materials for surfactant syntheses and for use as laundry aids. For example, their N-acylation and N-alkoxylation products can be used as surfactants in machine rinsing agents, as well as soil suspension agents in detergents. Of special interest is their use as textile-softening additives in anionic detergents.

The textile softening effectiveness of the compounds according to the invention in the presence of anionic surface active agents was not predictable from the state of the art and constitutes an unexpectedly advantageous property. The structurally closest prior art compounds are the reaction products of aldoses with long-chain primary amines and long-chain epoxides, and are known as softeners for cotton fabrics. However these prior art textile softeners are not very effective unless the compounds are added to the last rinse bath of the textiles to be treated. The textile softening results attainable with these known compounds in the wash bath are very slight. It was not to be expected that the minor modification of the N-substituent of the present compounds vis-a-vis the known compounds, could result in such a superior textile softening effectiveness in the wash bath by the present compounds.

The N-alkyl-N'-polyhydroxyalkyl-alkylene diamines softening agents are added to an aqueous washing liquor bath usually as a concentrated liquid such that the final amount ranges from 0.1 to 2.0 gm/liter of wash solution, and preferably from 0.2 to 1.0 gm/liter of wash solution. The anionic surface active agents and builder salts are added to the aqueous washing liquor bath such that the final total amount of both ranges from 0.1 to 3.0 gm/liter of wash solution, and preferably from 1.0 to 2.5 gm/liter of wash solution.

Of the synthetic anionic surface-active compounds, the sulfonates and sulfates possess special practical importance.

The sulfonates include, for example, the alkylaryl sulfonates, especially alkylbenzene sulfonates, which are obtained from preferably straight-chain aliphatic hydrocarbons having 9 to 15, especially 10 to 14 carbon atoms, by chlorinating and alkylating benzene or from corresponding terminal or non-terminal olefins by alkylation of benzene and sulfonation of the alkylbenzenes obtained. Further, aliphatic sulfonates are of interest, such as are obtainable, for example, from preferably saturated hydrocarbons containing 8 to 18 and preferably 12 to 18 carbon atoms in the molecule by sulfochlorination with sulfur dioxide and chlorine or sulfoxidation with sulfur dioxide and oxygen, and conversion of the products thereby obtained into the sulfonates. As aliphatic sulfonates, mixtures containing alkene sulfonates, hydroxyalkane sulfonates and disulfonates are useful, which are obtained from terminal or non-terminal $C_{8-18}$ and preferably $C_{12-18}$ olefins by sulfonation with sulfur trioxide and acid or alkaline hydrolysis of the sulfonation products. In the aliphatic sulfonates thus prepared, the sulfonate group is frequently found attached to a secondary carbon atom; however, sulfonates with a terminal sulfonate group obtained by reaction of terminal olefins with bisulfite can be used.

Furthermore, salts, preferably dialkali metal salts of α-sulfo-fatty acids, and salts of esters of these acids with mono- or poly-hydric alcohols containing 1 to 4, and preferably 1 to 2 carbon atoms belong to the sulfonates to be used according to the invention.

Further useful sulfonates are salts of fatty acid esters of hydroxyethanesulfonic acid or dihydroxypropane sulfonic acid, the salts of the fatty alcohol esters of lower aliphatic or aromatic sulfomono- or di-carboxylic acids containing 1 to 8 carbon atoms, alkylglycerylether sulfonates and the salts of the amide-like condensation products of fatty acids or sulfonic acids with aminoethane-sulfonic acid.

As tensides of the sulfate type are fatty alcohol sulfates, especially those prepared from coconut fat alcohols, tallow fat alcohols or oleyl alcohol. Useful sulfonation products of the sulfate type are also obtainable from terminal or non-terminal $C_{8-18}$ olefins. Sulfated fatty acid alkylolamides or fatty acid monoglycerides, and sulfated alkoxylation products of alkylphenols ($C_{8-15}$ alkyl), fatty alcohols, fatty acid amides or fatty acid alkylolamides, which may contain in the molecule 0.5 to 20, preferably 1 to 8 and especially 2 to 4 ethylene and/or propylene glycol residues, also belong to this group of surface-active compounds.

Suitable anionic surface active compounds of the carboxylate type are the fatty acid esters or fatty alcohol ethers of hydroxycarboxylic acids, and the amide-like condensation products of fatty acids or sulfonic acids with aminocarboxylic acids, for example, with glycocoll, sarcosin or protein hydrolysates.

Other suitable anionic surface active agents include the saponification products of alkali metal hydroxides with fatty acid mixtures of esters having from 12 to 26 carbon atoms, preferably from 16 to 22 carbon atoms.

Suitable builders are weakly acid, neutral and alkaline reacting inorganic or organic salts, especially inorganic or organic complex-foaming substances.

Useful, weakly acid, neutral or alkaline-reacting salts according to the invention are, for example, the alkali metal bicarbonates, carbonates, borates or silicates, mono-, di- or tri-alkali metal orthophosphates, di- or tetra-alkali metal pyrophosphates, alkali metal metaphosphates, pentaalkali metal triphosphates, known as complex-forming substances, alkali metal sulfates and the alkali metal salts of organic, non-surface-active sulfonic acids, carboxylic acids and sulfocarboxylic acids containing 1 to 8 carbon atoms. These include, for example, water-soluble salts of benzene-, toluene- or xylene-sulfonic acid, water-soluble salts of sulfoacetic acid, sulfobenzoic acid or salts of sulfodicarboxylic acids and the salts of acetic acid, lactic acid, citric acid and tartaric acid.

Further, the water-soluble salts of higher molecular weight polycarboxylic acids are utilizable as builders, especially polymerizates of maleic acid, acrylic acid, methacrylic acid, itaconic acid, mesaconic acid, fumaric acid, aconitic acid, methylene-malonic acid and citraconic acid. Co-polymerizates of these acids with one another or with other polymerizable substances, as for example, with ethylene, propylene, crotonic acid, 3-butene-carboxylic acid, 3-methyl-3-butenecarboxylic acid and with vinyl methyl ether, vinyl acetate, isobutylene, acrylamide and styrene, are utilizable.

Suitable complex-forming builders are also the weakly acid reacting metaphosphates and the alkaline reacting polyphosphates, especially tripolyphosphate, in the form of their alkali metal salts. They may be wholly or partly replaced by organic complex forming substances.

The organic complex-forming substances include, for example, nitrilotriacetic acid, ethylenediaminetetraacetic acid, N-hydroxyethyl-ethylenediaminetriacetic acid, polyalkylene-polyamine-N-polycarboxylic acids and other known organic complex-forming substances, while combinations of different complex-forming substances may also be used. Di- and poly-phosphonic acids of the following constitutions also belong to the other known complex-forming substances:

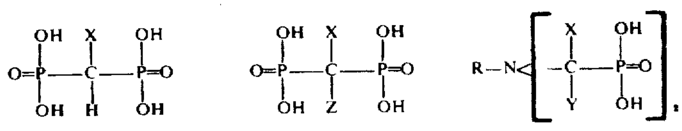

-continued

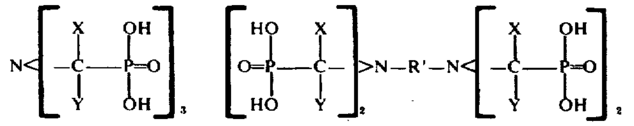

in which R represents alkyl and R′ alkylene radicals with 1 to 8, preferably 1 to 4 carbon atoms, X and Y represent hydrogen or alkyl radicals with 1 to 4 carbon atoms and Z represents —OH, $NH_2$ or NXR. For a practical application above all the following compounds are considered: methylene-diphosphonic acid, 1-hydroxyethane-1,1-diphosphonic acid, 1-aminoethane-1,1-diphosphonic acid, amino-tri-(methylene-phosphonic acid), methyl-amino- or ethylamino-di-(methylene-phosphonic acid) as well as ethylenediamino-tetra-(methylene-phosphonic acid). All these complexing compounds may be present as free acids or preferably as the alkali metal salts.

The following examples are merely illustrative of the present invention without being deemed limitative in any manner thereof.

EXAMPLE 1

186 gm (1 mol) of N-octyl-trimethylene diamine and 180 gm (1 mol) of glucose were dissolved in 500 ml of ethanol, and hydrogenated with vigorous stirring in an autoclave in the presence of 90 gm of Raney nickel. A hydrogen pressure of 180 atm was maintained; and the reaction times and temperatures were as follows: 2 hours at 50°C, 2 hours at 60°C, and lastly 2 hours at 90°C. The catalyst was separated from the hot ethanol solution; the product was crystallized out by cooling and subsequently recrystallized repeatedly from ethanol. The resulting product was a fine crystalline substance which had the melting point 126°C, and was white in color.

| Analysis: ($C_{17}H_{38}O_5N_2$) | C | H | N | O |
|---|---|---|---|---|
| Calculated | 58.26% | 10.39% | 7.99% | 22.82% |
| Found | 57.98% | 10.83% | 7.91% | 23.27% |
| OH number: | | | | |
| Calculated | 1,118 | | | |
| Found | 1,180 | | | |

EXAMPLES 2 to 6

Utilizing a procedure analogous to that described in Example 1, 1 mol of glucose was reacted with 1 mol of N-alkyl-trimethylene diamines of the chain lengths listed below to produce N-alkyl-N′-polyhydroxyalkyl-alkylene diamines, whose analytical characteristics are compiled in the following Table.

TABLE

| Example No. | 2 | 3 | 4 | 5 | 6 |
|---|---|---|---|---|---|
| Alkyl | $C_{10}H_{21}$ | $C_{12}H_{25}$ | $C_{14}H_{29}$ | $C_{16}H_{33}$ | $C_{18}H_{37}$ |
| M.p. (°C) | 119 | 122 | 119 | 102 | 108 |
| C calc. | 60.28% | 62.03% | 63.56% | 64.89% | 66.08% |
| found | 60.19% | 62.15% | 63.17% | 64.76% | 66.01% |
| H calc. | 11.18% | 11.40% | 11.59% | 11.76% | 11.91% |
| found | 10.96% | 11.64% | 11.99% | 12.04% | 12.07% |
| N calc. | 7.40% | 6.89% | 6.45% | 6.05% | 5.71% |
| found | 6.93% | 6.84% | 6.36% | 6.02% | 5.67% |
| O calc. | 21.13% | 19.67% | 18.40% | 17.29% | 16.30% |
| found | 21.60% | 19.13% | 18.91% | 17.30% | 16.48% |
| OH number calc. | 1,036 | 964 | 902 | 847 | 799 |
| found | 1,060 | 930 | 890 | 810 | — |

EXAMPLE 7

Utilizing a procedure analogous to that described in Example 1, 1 mol of glucose was reacted with 1 mol of N-coconut-alkyl-trimethylene diamine (mean chain length of the alkyl being 13.2 carbon atoms). After working up the product resulting therefrom was a white, fine crystalline substance, which had the melting point of 102° to 104°C and an OH number of 905 (calculated 926). The nitrogen content of the compound was determined titrimetrically to be 6.27% (calculated 6.61%).

EXAMPLE 8

A white, fine crystalline product produced in a manner analogous to that described in Example 1 from glucose and an N-tallow-alkyl-trimethylene diamine (mean alkyl chain length of 17.3 carbon atoms) had a melting point of 103° to 105°C, an OH number of 790 (calculated 815) and a titrimetrically determined nitrogen content of 5.63% (calculated 5.83%).

EXAMPLE 9

A wash solution was prepared which contained on a per liter basis 0.5 gm of a surfactant mixture consisting of 25 parts by weight of the sodium salt of n-dodecylbenzene sulfonate, 10 parts by weight of the sodium soap of a fatty acid mixture having 16 to 22 carbon atoms as follows: 8% $C_{16}$, 32% $C_{18}$, 12% $C_{20}$, 48% $C_{22}$, 15 parts by weight of sulfated adduct of 2 mols of ethylene oxide to 1 mol coconut fatty alcohol (Na salt), as well as 1.6 gm pentasodium triphosphate; and 0.4 gm of the products produced according to Examples 2, 3, 4 and 7.

With this wash solution, new desized cotton fabric was washed five times at a bath ratio of 1 part by weight of fabric to 25 parts by weight solution and at a laundering temperature of 50°C in a Launder-O-meter, intermediately rinsed after each washing operation, and dried. After the last washing and drying, the softness of the treated fabric was rated by a handle test which was carried out by four experienced test people. In the handle evaluation the grades 1 to 10 were given, with 1 denoting a very hard fabric, and 10 denoting a very soft fabric.

All fabrics treated with the substances according to the above-mentioned examples in the wash bath received the grade of 10.

Control fabric samples which had been treated using a washing agent of otherwise identical composition, but in which the textile softener had been replaced by the same quantity by weight of either sodium sulfate or N-dodecyl-N-(2-hydroxy-($C_{13}$ to $C_{16}$)-alkyl)-pentahydroxyhexylamine, received the grades 1 and 3, respectively, in the handle evaluation.

Fabric samples which had been treated in the same manner with the products produced according to Examples 5, 6 and 8 and reaction products from invert sugar and N-dodecyl ethylene diamine, N-hexadecyl ethylene diamine, and N-octadecyl ethylene diamine received the grades 8 to 9.

Although the present invention had been disclosed in connection with a few preferred embodiments thereof, variations and modifications may be resorted to by those skilled in the art without departing from the principles of the new invention. All of these variations and modifications are considered to be within the true spirit and scope of the present invention as dislosed in the foregoing description and defined by the appended claims.

I claim:

1. A compound of the formula $$R-NH-(CH_2)_n-NH-CH_2-(CHOH)_m-CH_2OH$$

in which R is an alkyl of 8 to 24 carbon atoms, *n* is an integer from 2 to 6, and *m* is an integer from 3 to 4.

2. A compound according to claim 1, wherein R is alkyl having 8 carbon atoms.

3. A compound according to claim 1, wherein R is alkyl having 10 carbon atoms.

4. A compound according to claim 1, wherein R is alkyl having 12 carbon atoms.

5. A compound according to claim 1, wherein R is alkyl having 14 carbon atoms.

6. A compound according to claim 1, wherein R is alkyl having 16 carbon atoms.

7. A compound according to claim 1, wherein R is alkyl having 18 carbon atoms.

* * * * *